(12) United States Patent
Takao et al.

(10) Patent No.: US 6,747,739 B2
(45) Date of Patent: Jun. 8, 2004

(54) OBSERVING TECHNIQUES AND ITS EVALUATION EQUIPMENTS OF FILLER PACKING-STRUCTURE FOR RESIN POLYMER COMPOSITE FILLED WITH CERAMIC FILLER-POWDER

(75) Inventors: Yasumasa Takao, Aichi (JP); Mutsuo Sando, Aichi (JP); Makio Naito, Aichi (JP); Keizo Uematsu, Niigata (JP)

(73) Assignee: Agency of Industrial Science and Technology, Tokyo (JP)

( * ) Notice: Subject to any disclaimer, the term of this patent is extended or adjusted under 35 U.S.C. 154(b) by 395 days.

(21) Appl. No.: 09/748,004

(22) Filed: Dec. 27, 2000

(65) Prior Publication Data

US 2002/0021442 A1 Feb. 21, 2002

(30) Foreign Application Priority Data

Aug. 16, 2000 (JP) ........................................ 2000-246644

(51) Int. Cl.$^7$ ............................. G01J 4/00; G01N 11/00
(52) U.S. Cl. ...................... 356/364; 356/366; 436/164; 436/171; 422/68.1; 422/82.05; 73/866
(58) Field of Search ................................. 356/364–369, 356/33–35; 250/225; 436/164, 171; 422/68.1, 82.05, 82.09; 73/866, 53.01, 54.01; 427/214, 228, 299, 379

(56) References Cited

U.S. PATENT DOCUMENTS 4,786,802 A * 11/1988 Yoshii et al. ................ 260/225
5,903,352 A * 5/1999 Ohsaki et al. ............... 356/364

OTHER PUBLICATIONS

Yasumasa Takao, et al. "Processing defects and their relevance to strength in alumina ceramics made by slip casting", Journal of the European Ceramic Society, vol. 20, 2000, pp. 389–395.

* cited by examiner

Primary Examiner—Hoa Q. Pham
(74) Attorney, Agent, or Firm—Oblon, Spivak, McClelland, Maier & Neustadt, P.C.

(57) ABSTRACT

This invention relates to a method of measuring the internal structure (packing structure or dispersion condition of particulate material) of a composite filled with particles having an irregular matrix by observations based on its optical anisotropy, in which the internal structure (packing structure or dispersion condition of particulate material) of the composite obtained by mixing particulate material as raw material with a liquid material is made visible by utilizing the photoelasticity based on local rearrangement of liquid material molecules or difference of refractive indices of the particulate material and liquid material, and the structure thereof are observed, and an evaluation device using this principle of measurement.

5 Claims, 5 Drawing Sheets

50 μm

OBSERVING TECHNIQUES AND ITS EVALUATION EQUIPMENTS OF FILLER PACKING-STRUCTURE FOR RESIN POLYMER COMPOSITE FILLED WITH CERAMIC FILLER-POWDER

BACKGROUND OF THE INVENTION

1. Field of the Invention

The present invention relates to a method and equipment for measuring the internal structure of a composite material filled with ceramic particles having an irregular matrix. In more particularly, it relates to a method in which the internal structure (packing structure or dispersion condition of the particles) of a composite material filled with ceramic particles obtained by mixing raw ceramic particles into a liquid material is measured by making this visible and observing it by utilizing the photoelasticity based on local rearrangement of liquid material molecules, or the difference of refractive index of the particles and liquid material, and to an evaluation device used therein.

2. Description of the Related Art

Composite materials filled with ceramic particles are employed as insulating materials, electrode/conductive materials, electroviscous fluids, chemical/mechanical grinding slurries, and raw materials for ceramic molding processes such as injection molding and/or cast molding, and also, in recent years, have come to be widely used in sealing materials intended for protecting and insulating semiconductor elements. With progress in VLSI, in order to achieve increased element fineness, low viscosity/high forming ability of composite material filled with ceramic particles in order to achieve the ability to produce any required shape and/or to enable pouring between minute electrodes is indispensable.

However, scientific study of the field of such materials is still in its infancy and studies relating to the viscosity and moldability of composite material filled with ceramic particles are based merely on experience. For example, it means that lower viscosity of the composite is sought to be achieved by making the particle size distribution of the particles to be filled larger or by making the particle size of the particles larger. It has been pointed out that there are limits to the extent to which it is possible to achieve the accuracy required in for example semiconductor sealing materials simply using such conventional discoveries (for example, Shinsuke Hagiwara "The present state of development of semiconductor sealing materials", Plastics, Vol. 49, p. 58, 1998 and Takeshi Kitano "Rheological properties of molten polymer solution filled with filler", Filler, Vol. 3, p. 96, 1998).

A typical method of "directly" evaluating the distribution condition of a particular material filled/dispersed in a composite material is the method in which some of the dispersed material is collected and its surface is polished and the reflected image thereof is observed by using an optical microscope or scanning electron microscope (SEM). For example, Laid-open Japanese Patent Publication Number 10-292055 (1998) discloses the former method using an SEM and in Laid-open Japanese Patent Publication Number 9-302210 (1997) an optical microscope method is applied to evaluation of uniformity of particle dispersion. However, with such methods, there is the risk of altering the distribution condition of the particles by the surface processing and, in addition, the information obtained is restricted to that from the reflection surface of the light from the light source i.e. to 2-dimensional information, so the distribution condition of the particulate material could not be evaluated directly over a wide region.

As a method of direct evaluation similar to the above, there is the method of observing the transmitted image by producing a thin strip of thickness capable of transmitting light from the light source. For example, Laid-open Japanese Patent Publication Number 61-122543 (1986) and Laid-open Japanese Patent Publication Number 5-232010 (1993) disclose methods using the transmitted image obtained by an optical microscope. With these methods, the problem of adverse effects due to processing and 2-dimensional observation is solved. In fact, by means of these methods, it is possible to recognize the packed particulate material itself. However, by using these on their own it is not possible to evaluate the bonding condition at the interface between the particles and the resin or the coagulation condition that is secondarily constituted within the interior of the dispersion system by the particles. The dominant factors in regard to rheological properties of a resin polymer composite filled with particles, which are currently becoming even more vital, are considered to be interactions at the particle/resin interface and the resin constituents within coagulations thereof. Evaluation of these is indispensable but, with previous methods, as will be described in detail with reference to the examples below, it has not been possible to achieve this.

As a method of evaluating a composite filled with particles in comparatively large volume that supplemented the defects of the reflection observation method, there was the method of indirectly deducing the distribution condition of the particulate material by measuring for example the coefficient of viscosity, electrical resistance or tensile strength of the dispersion system. For example, Laid-open Japanese Patent Publication Number 6-229984 (1994) and Laid-open Japanese Patent Publication Number 11-64260 (1999) are examples of a method of measuring electrical resistance and Laid-open Japanese Patent Publication Number 10-311783 (1998) is an example of a method of measuring tensile strength. Even such methods were insufficient to obtain local information such as the interactions at the particle/resin interface or the particle coagulation structure.

One cause of the above problem is considered to be that no method has been established for observing the internal structure of a dispersed system and correlating this with mechanical properties/rheological properties/electrical properties etc. of the dispersion system in cases where the liquid material is a matrix or dispersion medium. For example, one problem is considered to be that no methodology has been established for the application of methods of measurement using an optical microscope or scanning electron microscope (SEM), which are universal in regard to dispersion systems where the dispersion medium of the particulate material is solid (for example ceramic material systems) to composite material filled with particles having an irregular matrix. Even where the matrix is a solid dispersion system, studies based on such a viewpoint have only just been commenced.

Conventionally, in addition to the risk of altering the distribution condition of the particles by surface processing methods using an SEM, the information obtained was restricted to the reflection surface of the light from the light source i.e. was only 2-dimensional information and so could not be used to evaluate the distribution condition of the particulate material directly in a region. In this regard, a method has been proposed for performing evaluation using transmission images utilizing the difference of refractive index etc. at the interface between particulate material and gas bubbles contained within the dispersion system (K. Uematsu, "Immersion microscopy for detailed characterization of defects in ceramic powders and green bodies", Powder Technology, Vol. 88, p. 291, 1996). With this method, the problems of adverse effects due to processing and 2-dimensional observation are solved. Establishment of a similar method for evaluation in regard to liquid materials filled with particles is indispensable.

The case when the liquid material in a liquid material filled with particles.dispersion system is a resin-based material can be regarded as one type of polymer material. In polymeric material systems, typically use is made of polarized light observation for evaluation of the photoelasticity characteristic with applied stress, measurement of the birefringence of a plastic lens, or evaluation of molecular alignment characteristics in liquid crystal materials. However, previously, no attempts have been made to employ this for evaluation of the characteristics of particles, rather than resin, in resin filled with particles.dispersion materials. The reason for this is believed to be that the particulate materials that are generally employed in this material field are (amorphous) $SiO_2$ particles and it was not intuitively anticipated that these methods of observation could be applied to materials having an isotropic crystalline structure (or not having a crystalline structure).

In order to overcome the defects possessed by such conventional measurement techniques for composite materials filled with particles, the present invention was developed taking as technical problem the provision of a method of measurement of the internal structure (packing structure or dispersion condition of the particulate material) of particulate material in the composite materials and evaluation equipment employing this principle of measurement by visualization and observation utilizing the photoelasticity based on local rearrangement of liquid molecules and the difference of refractive indices of the particulate material and liquid material.

The inventors have noted an evaluation technique for photoelasticity or optical anisotropy that is conducted with polymeric materials. Specifically, the present inventors, having in mind that, in preparing a composite material filled with particles, if the packing structure of the particulate material was non-uniform or secondary coagulations were created, this would apply stress to the surrounding liquid material, increasing the alignment of polymer molecules etc. compared with locations where this did not apply, and would generate gas bubbles at interface regions of the particulate material and liquid material, or that the interface itself (connected surface comprising different refractive indices) comprising materials of different kinds would constitute an optically anisotropic body, and that these would have optical distortion enabling them to be evaluated by diagonal position observation, as a result of meticulous study aimed at implementing the above concept and various studies concerning the primary properties of particles such as particle size distribution of the particulate material serving as filler and the effect of method of preparation and the condition of the evaluation sample, discovered that the packing structure and/or dispersion condition of the particulate material could be identified by using such optical anisotropy and perfected the present invention based on this discovery.

SUMMARY OF THE INVENTION

A method of measuring the internal structure (packing structure or dispersion condition of the particulate material) of a composite filled with particles, wherein the drawbacks possessed by the conventional measurement technique for composite materials filled with particles are ameliorated. This invention relates to a method of measuring the internal structure (packing structure or dispersion condition of particulate material) of a composite filled with particles having an irregular matrix by observations based on its optical anisotropy, in which the internal structure (packing structure or dispersion condition of particulate material) of the composite obtained by mixing particulate material as raw material with a liquid material is made visible by utilizing the photoelasticity based on local rearrangement of liquid material molecules or difference of refractive indices of the particulate material and liquid material, and the structure thereof are observed, and an evaluation device using this principle of measurement. This makes it possible to provide a technique or evaluation device for observing the internal structure (packing structure or dispersion condition of particulate material) of a composite filled with particles wherein the liquid material is a matrix or dispersion medium, and in particular is ideal as a technique for structural analysis or a technique for manufacturing process control of insulating materials or semiconductor sealing materials in which there is a great need to identify the internal structure.

DETAILED DESCRIPTION OF THE INVENTION

An object of the present invention is to provide a method and evaluation equipment used therein for measuring the internal structure constituted by the packing structure and/or dispersion condition of the particulate material in a composite material filled with particles having an irregular matrix obtained by mixing a particulate material as raw material with a liquid material by utilizing the photoelasticity effect of the liquid material and/or the optical anisotropy etc. possessed by the particle/liquid interface.

In order to realize the above object, according to the present invention, the following constitution is adopted:

(1) A method of measuring the internal structure (packing structure or dispersion condition of particulate material) of a composite material filled with ceramic particles having an irregular matrix by observations based on its optical anisotropy, which comprises mixing particulate material as raw material with a liquid material to obtain a composite material filled with ceramic particles, making visible the internal structure (packing structure or dispersion condition of particulate material) of the composite material by utilizing the photoelasticity based on local rearrangement of liquid material molecules or difference of refractive indices of the particulate material and liquid material, and then observing the structure.

(2) The method of measuring the internal structure of a composite material filled with ceramic particles according to (1) above, wherein the particulate material is an $SiO_2$ based material or AlN based material.

(3) The method of measuring the internal structure of a composite material filled with ceramic particles according to (1) above, wherein the liquid material is a resin based material.

(4) Equipment for evaluation used in the method of measurement claimed in any of (1) to (3) above, which comprises as structural elements two polarizing elements, a light source or electron beam source, means for observing a transmitted image, and means for arranging a sample, wherein a thin strip sample for transmission observation is arranged between the two polarizing elements, monochromatic light polarized by the first polarizing element is directed onto the sample, and subjected to double refraction at optically anisotropic regions such as coagulations in the sample, then re-polarized by the second polarizing element, and observed by the transmitted image observation means to evaluate optical behavior thereof such as diagonally opposite positions or interference.

(5) The evaluation equipment according to (4) above, wherein the sample is a composite material filled with particles converted to the form of a thin strip of a thickness allowing monochromatic light from a light source or electron beam source to be transmitted through the composite material.

(6) The evaluation equipment according to (4) above, wherein halogen light is directed on the sample.

DESCRIPTION OF THE PREFERRED EMBODIMENTS

Figure 1A:
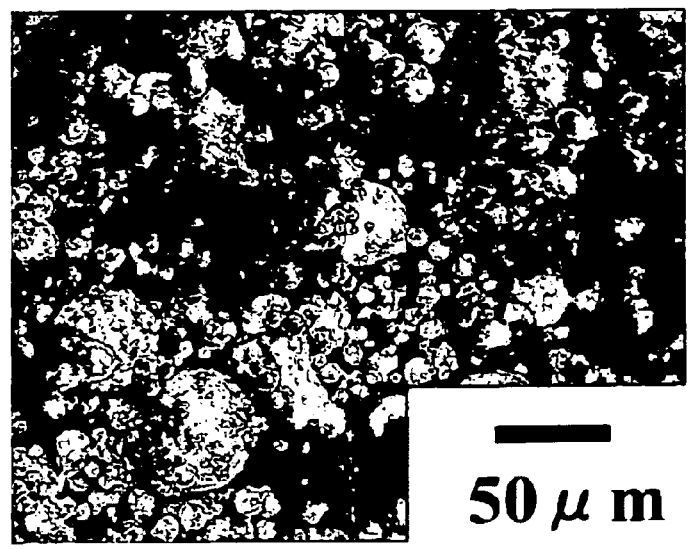
FIGS. 1a, 1b shows an SEM photograph of amorphous/spherical $SiO_2$ particles of two types of particle size distribution.

The invention is described in further detail below.

The chief feature of the present invention consists in the use of an optical anisotropy signal of the composite filled with particles. For example $SiO_2$ or AlN, which are commonly used in sealing materials for semiconductor elements, may suitably be employed as the particulate material according to the present invention; apart from these, for example $Al_2O_3$, SiC, $Si_3N_4$ or other oxides, or metals such as Au, Ag, Pd, Pt, Cu, Al, or Au—Pd may of course be employed without any particular restriction. Also, there is no restriction concerning crystallinity; evaluation can be performed easily for crystalline particles or as described above even for amorphous systems.

As the liquid material constituting the medium, suitable examples that may be given include water such as ionized water or distilled water, organic non-aqueous materials such as ethanol and, in addition, resins such as for example resol-type or novolak-type phenolic resins, bisphenolic cresol-novolak multi-functional type epoxy resins, halogenated resins etc., resin materials of the type that are solid at ordinary temperature, and resin materials of liquid type at ordinary temperature that are commonly used as sealing materials for second generation semiconductor elements may suitably be employed; but there is no particular restriction to these.

As the method of preparing the composite filled with particles, various types of compounding techniques etc. such as for example methods of mixing using a kneader, biaxial mill, 3-roll mill, Henschel mixer or planetary motion, mechanical compounding methods using pulverization and/or shearing stress (solid phase methods), liquid phase methods using uniform dispersion of a plurality of constituents in a liquid, or gaseous phase methods using inertial force etc. in a gas maybe employed without any particular restriction: the present invention may be applied to composite materials filled with particles prepared by any of these methods.

As a specific example of a composite filled with particles to which the present invention may be applied, there may be mentioned semiconductor sealing material tablets formed by premixing of $SiO_2$ particles of weight ratio 70 to 90% (with respect to the liquid material) and novolak-based phenolic resin with plasticiser, followed by kneading in a kneader heated to 150 to 180° C. to produce a plate-shaped composite molding, which is then pulverized to obtain a granular powdered raw material which is molded into pellets.

The internal structure (packing structure or dispersion condition of the particulate material) of the composite filled with particles obtained is observed by optical reflection or transmission. Technical features for this purpose may basically include a light source and/or electron beam source directed onto the material, a polarizing element, means for observing reflected or transmitted images, or sample arrangement means etc. but may be of any constitution provided they can achieve measurement of optical anisotropy of for example reflected or transmitted light from the composite filled with particles. A convenient method that does not require adjustment of atmosphere etc. which may be mentioned is for example a method wherein a thin strip sample for transmission observation is arranged between two polarizing elements and monochromatic light is polarized by the first polarizing element and directed onto the sample, where it is subjected to double refraction at optically anisotropic regions such as coagulations in the sample, before being re-polarized by the second polarizing element, wherein optical behavior such as the diagonally opposite positions or interference is measured and evaluated; however, there is no particular restriction thereto.

When transmission observation is employed, the composite filled with particles is converted to the form of a thin strip sample. The technical conditions when this is done are that the sample is made of a thickness capable of transmitting monochromatic light from the light source or electron beam source that is employed; there are no particular restrictions regarding the method.

Figure 5:
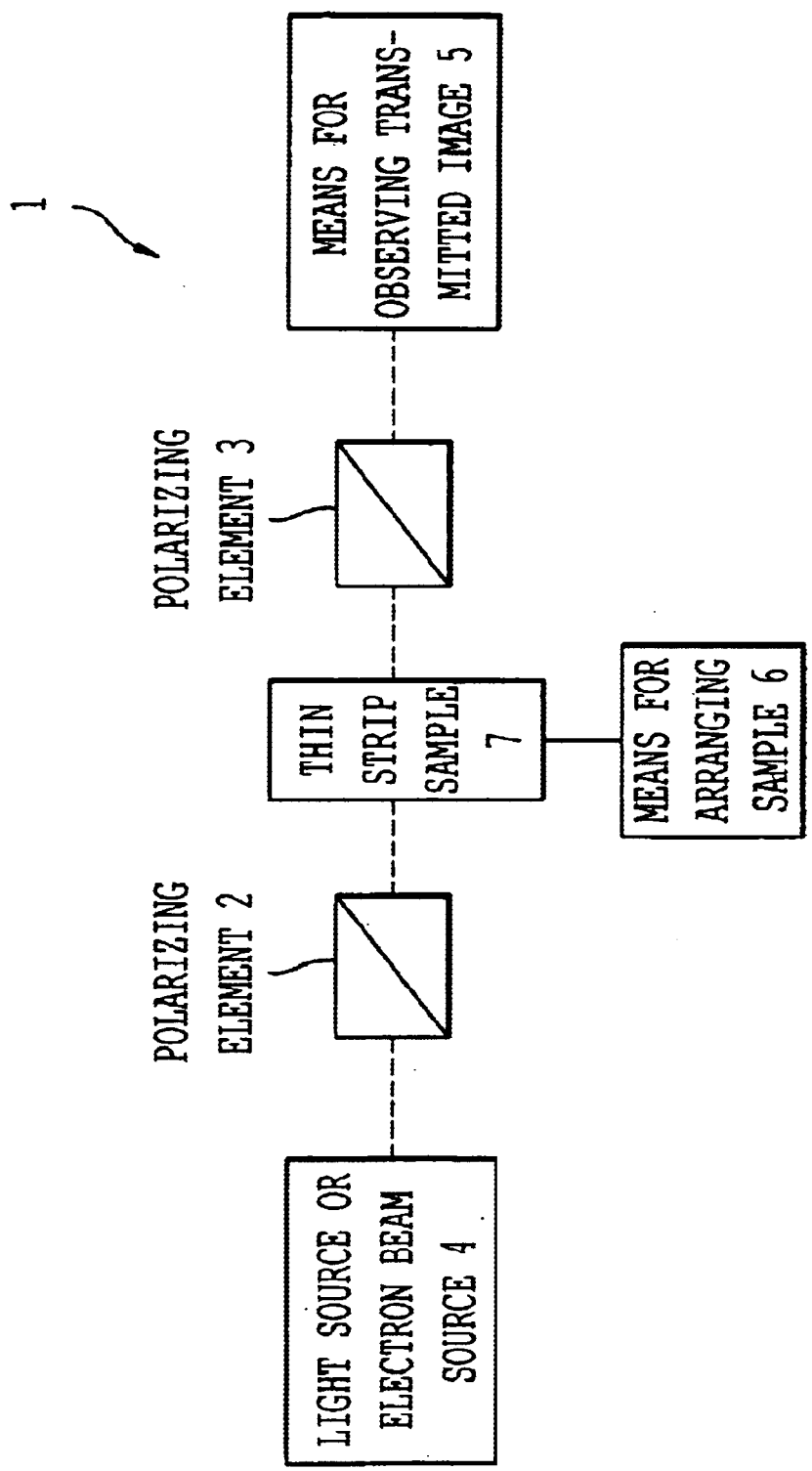
FIG. 5 shows a device for evaluating optical behavior of a composite material.

As a specific example of a construction of the equipment employed in the measurement method of the present invention, there may be mentioned, as shown in FIG. 5, an example construction comprising a device 1 for evaluating optical behavior such as diagonally opposite positions and/or interference including as structural elements two polarizing elements 2, 3, a light source or electron beam source 4, means for observing a transmitted image 5, and means for arranging a sample 6, in which a thin strip sample 7 for transmission observation is arranged between the two polarizing elements 2, 3, monochromatic light polarized by the first polarizing element 2 is directed onto the sample 7, and subjected to double refraction at optically anisotropic regions such as coagulations in the sample 7, then re-polarized by the second polarizing element 3 and observed by the transmitted image observation means 5. There may also be mentioned a device for observing the composite filled with particles which has been processed into the form of a sheet by fine adjustment of the amount of polarization by a polarizing microscope; and means whereby, after kneading in a kneader in the aforesaid semiconductor sealing material tablets manufacturing process, or in a production line after molding to pellet form, this subjected to in situ measurement by arranging a polarizing element as a measurement device, and is evaluated without destroying the tablet, and only defective products are removed.

EXAMPLES

Next, a specific description of the present invention is given with reference to examples thereof; however, the present invention is not restricted in any way by the following examples.

Examples (1) Method

Figure 1B:
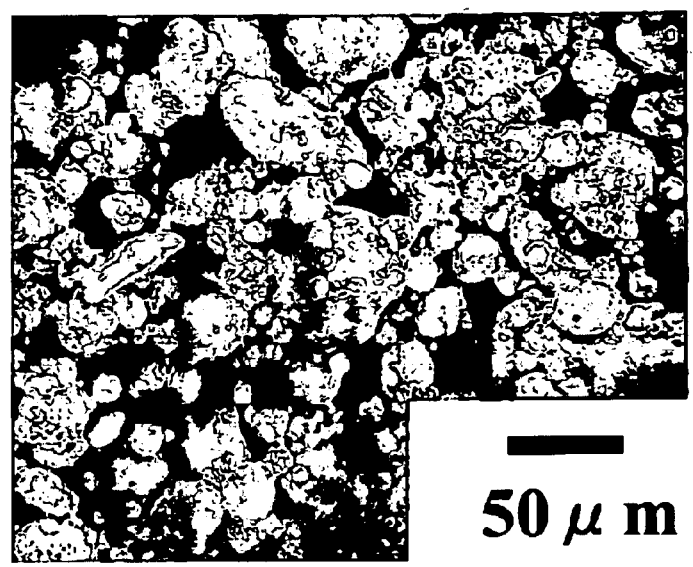
Figure 2:
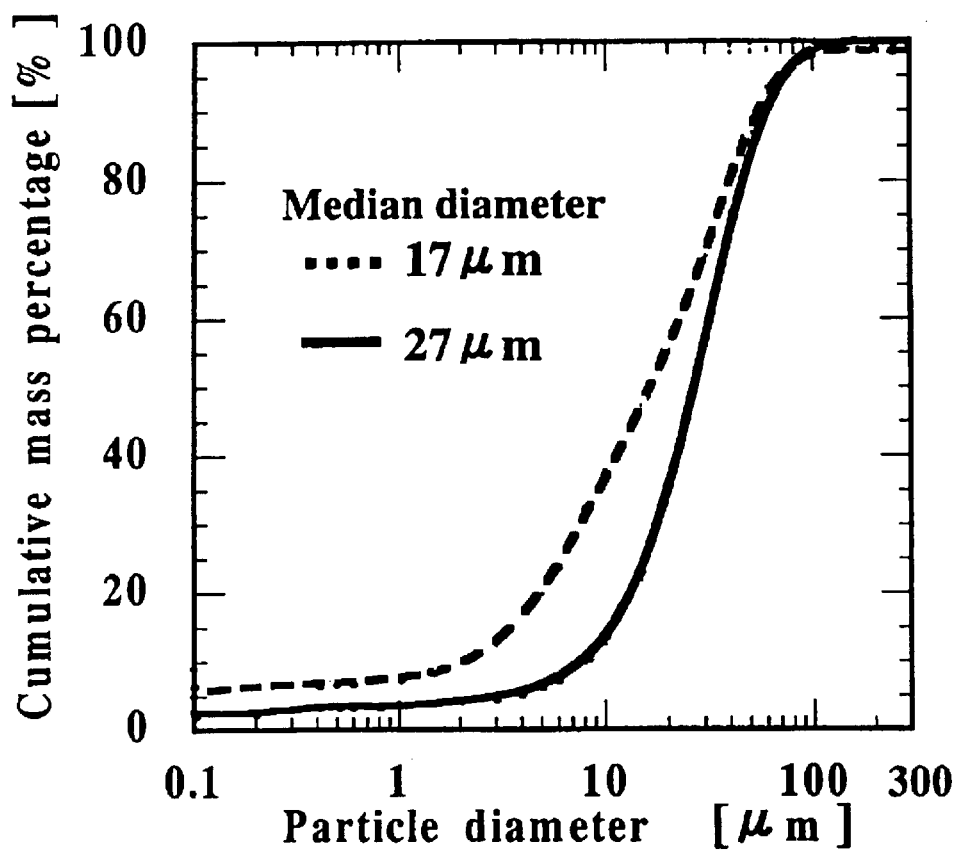
FIG. 2 shows the particle size distribution of the amorphous/spherical $SiO_2$ particles employed in the examples.

There were provided for testing amorphous/spherical $SiO_2$ particles having two types of particle size distribution, of mean particle size between 10 or more and several tens of $\mu$m and manufactured in a process of melting commonly-used silicon oxide raw material. FIGS. 1 and 2 show SEM photographs of particles of wide particle size distribution (FIG. 1-a)) and particles of narrow particle size distribution (FIG. 1-b)), and their particle size. With the particles of wide particle size distribution, materials can be manufactured in which the optical anisotropy of coagulations etc. is less than in the case of particles of narrow particle size distribution, since small particles can be packed between particles of large particle size when mixed with resin-based material in equal quantities.

A resin composite filled with particles was prepared by mixing these respective $SiO_2$ particles with bisphenol A type liquid epoxy resin in a weight ratio of 70% of the particles with respect to the resin, and kneading for five minutes with a rate of revolution of 1800 rpm and rate of rotation of 600 rpm to produce a resin composite filled with particles. Samples were manufactured by converting the resin composite filled with particles obtained into the form of thin strips of about 50 $\mu$m and transmission/polarization images were observed by arranging these between two polymer polarization plates and passing halogen light therethrough.

(2) Results

Figure 3A:
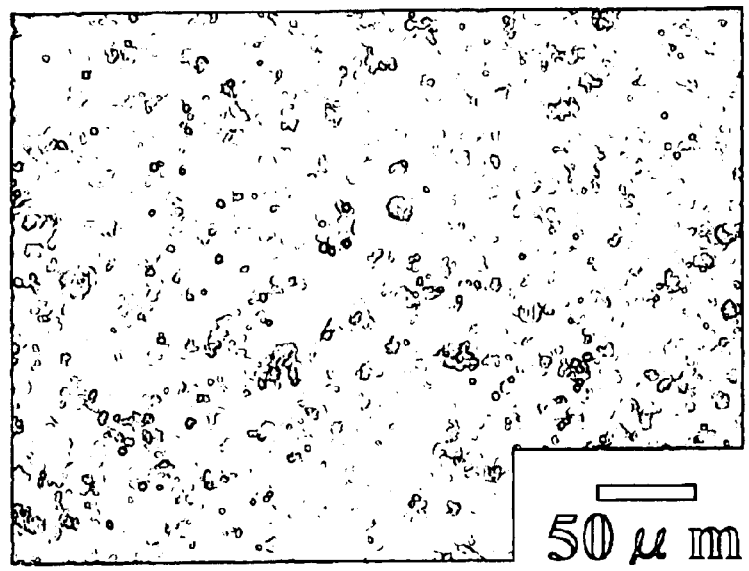
FIGS. 3a,b shows a transmission image of a resin composite filled with particles.dispersion material obtained using ordinary light.
Figure 3B:
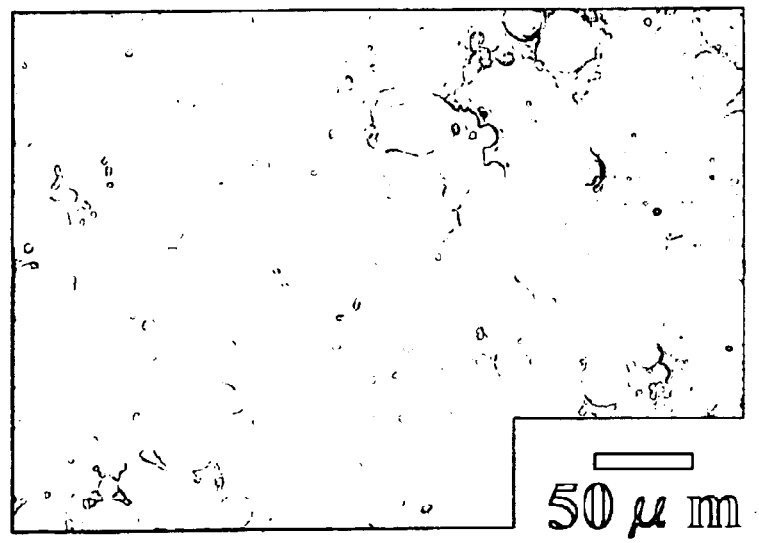

FIG. 3 shows an example of a resin composite filled with particles distribution system transmission image obtained using ordinary light (a): using particles of wide particle size distribution, b): using particles of narrow partcle size distribution). Although differences in the size of the particles packed in the resin composite filled with particles distribution material can be recognized, these are not clear in regard to the particle/resin interface or coagulations, so evaluation can only be carried out in regard to the former.

Figure 4A:
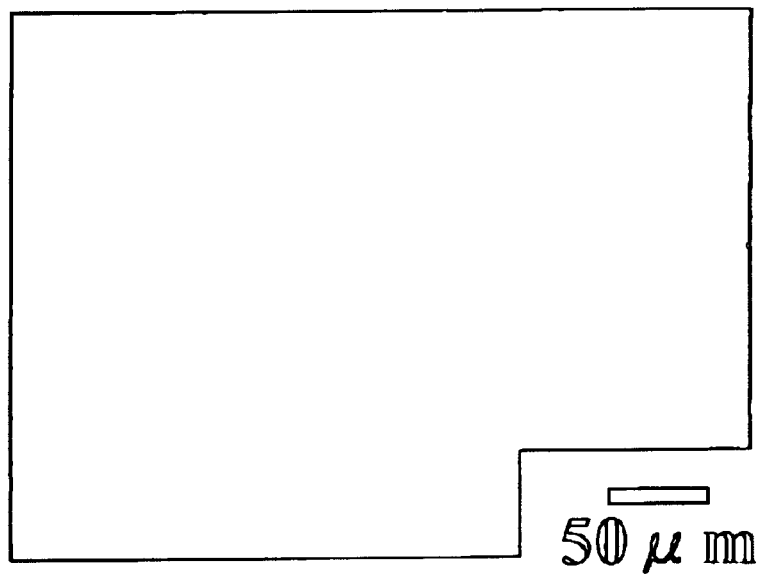
FIGS. 4a,b shows a transmission/polarization image of a resin composite filled with particles.dispersion material.
Figure 4B:
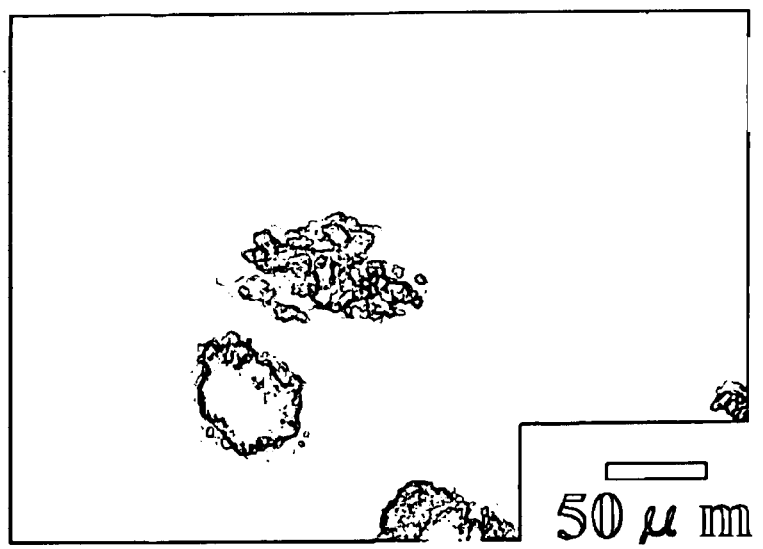

FIG. 4 shows example transmission/polarization images using the method of the present invention (a): using particles of wide particle size distribution, b): using particles of narrow partcle size distribution). In the case of the resin composite filled with particles distribution system of particles with a wider particle size distribution, it can be seen that the optical anisotropy detected as bright white portions was comparatively small (FIG. 4a)). However, in the case of the resin composite filled with particles distribution system of particles with a narrower particle size distribution it was found that many bright locations were detected and locations of optical anisotropy such as coagulations of particulate material could be evaluated (FIG. 4b).

According to the present invention, the noteworthy benefits are presented that 1) the internal structure (packing structure or dispersion condition of particulate material) of a composite filled with particles having an irregular matrix can be made visible and observed and measured, 2) for example the condition of distribution of fine particles in epoxy resin can be visualized, 3) the packing structure and/or dispersion condition of particulate material contained in a resin composite filled with particles can be observed in situ, 4) there can be provided a method and evaluation equipment whereby measurement can be performed in the natural condition of the dispersion system i.e. without subjecting the resin composite filled with particles to processing, and 5) it is well suited in particular as a method of evaluating semiconductor sealing materials.

What is claimed is:

1. A method of measuring the internal structure of a composite material filled with ceramic particles having an irregular matrix by observations based on its optical anisotropy, which comprises mixing particulate material as raw material with a liquid material to obtain a composite material filled with ceramic particles, making visible the internal structure of the composite material by utilizing the photoelasticity based on local rearrangement of liquid material molecules or the difference of refractive indices of the particulate material and liquid material, and then observing the internal structure, wherein the internal structure of the composite material is the packing structure or dispersion condition of the particulate material in the composite material.

2. The method according to a claim 1, wherein the particulate material is an $SiO_2$ based material or AlN based material.

3. The method according to claim 1, wherein the liquid material is a resin based material.

4. Equipment for evaluation used in the method of measurement claimed in any one of claims 1 to 3, which comprises as structural elements two polarizing elements, a monochromatic light source or electron beam source, means for observing a transmitted image, a thin strip sample for transmission observation arranged between the two polarizing elements and comprising a composite material containing ceramic particles in a liquid matrix, and means for arranging the sample, wherein monochromatic light polarized by the first polarizing element is directed onto the sample, and subjected to double refraction at optically anisotropic regions, then re-polarized by the second polarizing element, and observed by the means for observing a transmitted image to evaluate optical behavior thereof.

5. The equipment according to claim 4, wherein halogen light is directed on the sample.

* * * * *

UNITED STATES PATENT AND TRADEMARK OFFICE
CERTIFICATE OF CORRECTION

PATENT NO. : 6,747,739 B2
DATED : June 8, 2004
INVENTOR(S) : Takao et al.

It is certified that error appears in the above-identified patent and that said Letters Patent is hereby corrected as shown below:

<u>Title page,</u>
Item [73], Assignee, should read:
-- [73] Assignee: Japan as represented by Secretary of Agency of Industrial Science and Technology, Tokyo (JP) --

Signed and Sealed this

Twenty-third Day of November, 2004

JON W. DUDAS
*Director of the United States Patent and Trademark Office*